United States Patent [19]

Jones et al.

[11] Patent Number: 5,648,529
[45] Date of Patent: Jul. 15, 1997

[54] PROCESS FOR THE RECOVERY OF AN ORGANIC ACID FROM THE MANUFACTURE OF A CELLULOSE ESTER

[75] Inventors: Stephen C. Jones, Charlotte, N.C.; Denis G. Fallon, Rock Hill, S.C.

[73] Assignee: Hoechst Celanese Corporation, Somerville, N.J.

[21] Appl. No.: 442,044

[22] Filed: May 16, 1995

[51] Int. Cl.$^6$ .................................................. C07C 51/42
[52] U.S. Cl. .................................................. 562/608
[58] Field of Search ........................................ 562/608

[56] References Cited

U.S. PATENT DOCUMENTS

| 4,110,372 | 8/1978 | Hey et al. | 260/540 |
| 4,234,719 | 11/1980 | Wan | 536/69 |
| 4,435,595 | 3/1984 | Agreda et al. | 560/234 |
| 5,258,560 | 11/1993 | Marker | 568/697 |

OTHER PUBLICATIONS

Amberlyst® 35 and Amberlyst® 36 Resins High Performance Catalysts from Rohm and Haas Company of Philadelphia, PA, 1989.
Amberlyst® 36 Wet Polmeric Catalyst from Rohm and Haas Company of Philadelphia, PA, 1992.
Degarmo et al., "Consider Reactive Distillation", Chemical Engineering Progress, Mar. 1992, pp. 43–50.
Agreda, V.H. et al., "High–Purity Methyl Acetate via Reactive Distillation", Chemical Engineering Progress, Feb. 1990 pp. 40–46.

*Primary Examiner*—José G. Dees
*Assistant Examiner*—Rosalynd Williams
*Attorney, Agent, or Firm*—Robert H. Hammer, III; Miles B. Dearth

[57] ABSTRACT

The present invention is directed to a process for the recovery of an organic acid. The organic acid is generated from the manufacture of a cellulose ester. The first step of the process is to remove the organic acid from the manufacture of cellulose ester. The acid is in the form of a weak acid stream comprising of the organic acid and water. The weak acid stream is resolved, via a solvent extraction, to form an extractor overhead stream and raffinate stream. The raffinate stream comprises solvent, water, and alcohol. The alcohol is produced in the recovery process by hydrolysis of the solvent after the solvent extraction. The raffinate stream is resolved into a overhead stream and a bottom stream. The overhead stream comprises water, alcohol, and solvent. Excess organic acid is added to the overhead stream to form a feed stream. The feed stream is catalyzed, via ion exchange resins, whereby a portion of the alcohol is esterified to the solvent. The solvent, thus produced, is recycled into the recovery process.

8 Claims, 2 Drawing Sheets

PROCESS FOR THE RECOVERY OF AN ORGANIC ACID FROM THE MANUFACTURE OF A CELLULOSE ESTER

FIELD OF THE INVENTION

This invention is directed to a process for the recovery of an organic acid from the manufacture of a cellulose ester wherein alcohol, formed by hydrolysis of the solvent used in the recovery of the acid, is esterified, via an ion exchange catalyst, to the solvent.

BACKGROUND OF THE INVENTION

In the manufacture of cellulose esters, the recovery of the organic acid is very important. For example, in the manufacture of cellulose acetate, approximately 4 to 4½ kilograms (kg) of acetic acid are used per 1 kg of cellulose acetate produced. About ½ kg of acetic acid is consumed in the production of 1 kg of cellulose acetate and the remaining 3½ to 4 kg are discharged from the process. This discharged acetic acid is recovered and recycled into the cellulose acetate manufacturing process.

The principal unit operation in the recovery of the acetic acid, which is in the form of an aqueous weak acid stream comprising approximately between 25–35% by weight of acetic acid, is a liquid—liquid or solvent extraction process. Benzene was formally a component of the extraction liquor. However, concern, regarding the carcinogenic effects of benzene, has caused its use to be curtailed. In its place, new extraction solvents, including ketones, esters, ethers, and alkanes that have a boiling point less than acetic acid, are being evaluated and used when deemed appropriate. With the reformulation of the solvent, the prior processes, which included benzene, have been changed.

One problem that has arisen with the use of these new solvents, particularly the esters (e.g., ethyl acetate and isopropyl acetate), is its hydrolysis to alcohol (e.g., ethyl alcohol and isopropyl alcohol). This hydrolysis occurs principally in the portion of the acid recovery process after the solvent extraction where the solvent and the acetic acid are resolved, typically a distillation process.

This alcohol has a negative impact on the acid recovery process. When the alcohol reaches a concentration of about 2% by weight of the solvent stream, the liquid—liquid equilibrium (LLE) in the extractor is upset. This is manifested by increased water concentration in the extractor overhead stream. Increased water concentration is undesirable for two reasons: 1) the time between cleanings of the solvent/acetic acid distillation system is decreased because more organic salts are carried to it; and 2) the energy demand at the solvent/acetic acid distillation system is increased.

A prior solution to the increased level of alcohol in the solvent stream has been to distill out the alcohol and dispose of it through conventional waste water treatment systems. This solution, however, has two drawbacks: 1) the alcohol is wasted; and 2) the effluent stream carrying the alcohol causes a high chemical oxygen demand (COD) on the waste water treatment facility.

Another consideration limiting options to the solution of the alcohol problem are minor ion forming contaminants in the acid recovery process. These contaminants can form ions that poison ion exchange resins, and thereby limit the use of those resins. For example, acetonitrile will hydrolyze to form acetic acid and ammonium ions. Thus, the use of ion exchange resins in a solution of the problem is suspect.

Accordingly, in view of the above considerations, there is a need to reduce the alcohol level in the solvent stream of these acid recovery processes which: will not impact the liquid—liquid equilibrium of the extractor; will not place unnecessary demands on the waste water treatment facilities associated with the process; and can tolerate the ions generated by the process.

SUMMARY OF THE INVENTION

The present invention is directed to a process for the recovery of an organic acid. The organic acid is generated from the manufacture of a cellulose ester. The first step of the process is to remove the organic acid from the manufacture of cellulose ester. The acid is in the form of a weak acid stream comprising the organic acid and water. The weak acid stream is resolved, via a solvent extraction, to form an extractor overhead stream and raffinate stream. The raffinate stream comprises solvent, water, and alcohol. The alcohol is produced in the recovery process by hydrolysis of the solvent after the solvent extraction. The raffinate stream is resolved into a overhead stream and a bottom stream. The overhead stream comprises water, alcohol, and solvent. Excess organic acid is added to the overhead stream to form a feed stream. The feed stream is catalyzed, via ion exchange resins, whereby a portion of the alcohol is esterified to the solvent. The solvent, thus produced, is recycled into the recovery process.

DESCRIPTION OF THE DRAWINGS

For the purpose of illustrating the invention, there is shown in the drawings a form which is presently preferred; it being understood, however, that the invention is not limited to the precise arrangement and instrumentalities shown.

DETAILED DESCRIPTION OF THE INVENTION

Solvent, as used herein, refers to an extraction solvent for use in a liquid extraction of an organic acid from water, and to an ester. These solvents are components of the extraction liquor. Various components of the extraction liquors used for the acid recovery process associated with the manufacture of cellulose acetate include: organic esters (e.g., methyl acetate, ethyl acetate, isopropyl acetate); ketones; alkanes; ethers; benzene; and combinations thereof that have a boiling point less than the organic acid.

Alcohol, as used herein, refers to the hydrolysis product of the solvent. Exemplary alcohols include: methanol, ethanol, isopropyl alcohol, and mixtures thereof.

Cellulose ester, as used herein, refers to cellulose acetate (i.e., cellulose not completely esterified by acetic acid); cellulose diacetate; cellulose triacetate; cellulose acetate butyrate; cellulose acetate propionate; and the like. Cellulose acetate is preferred.

Ion exchange resins, as used herein, refer to synethic resins containing active groups (usually sulfonic, carboxylic, phenolic, or substituted amino groups) that give the resin the property of combining with or exchanging ions between the resin and a solution. Such resins should be strongly acidic. A solid resin having sulfonic groups is preferred. Such resins are commercially available; for example: AMBERLYST® 35; AMBERLYST® 36; AMBERLYST® 16; AMBERLYST® 15 resins from Rohm and Haas Company of Philadelphia, Pa.

Hydrolysis, as used herein, refers to the chemical reaction by which an ester and water are reacted, typically in the presence of a strong acid catalyst, to form an alcohol and an organic acid. The following formula is exemplary of hydrolysis:

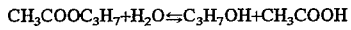

$$CH_3COOC_3H_7 + H_2O \rightleftharpoons C_3H_7OH + CH_3COOH$$

Esterification, as used herein, refers to the chemical reaction by which an alcohol and an organic acid are reacted, typically in the presence of a strong acid catalyst and an excess of the organic acid, to form an ester and water. The following formula is exemplary of esterification:

$$C_2H_5OH + CH_3COOH \rightleftharpoons CH_3COOC_2H_5 + H_2O$$

Packing, as used herein, refers to tower packing or tower filling which are solid inert shapes used in a column to facilitate mass transfer (i.e., inert packing), and may contain catalyst (i.e., catalytic packing). Such packing is commercially available; for example: inert packing-SULZER packing from Koch Engineering Co., Wichita, Kans.; and catalytic packing-KATAMAX® packing from Koch Engineering Co., Wichita, Kans.

Figure 1:
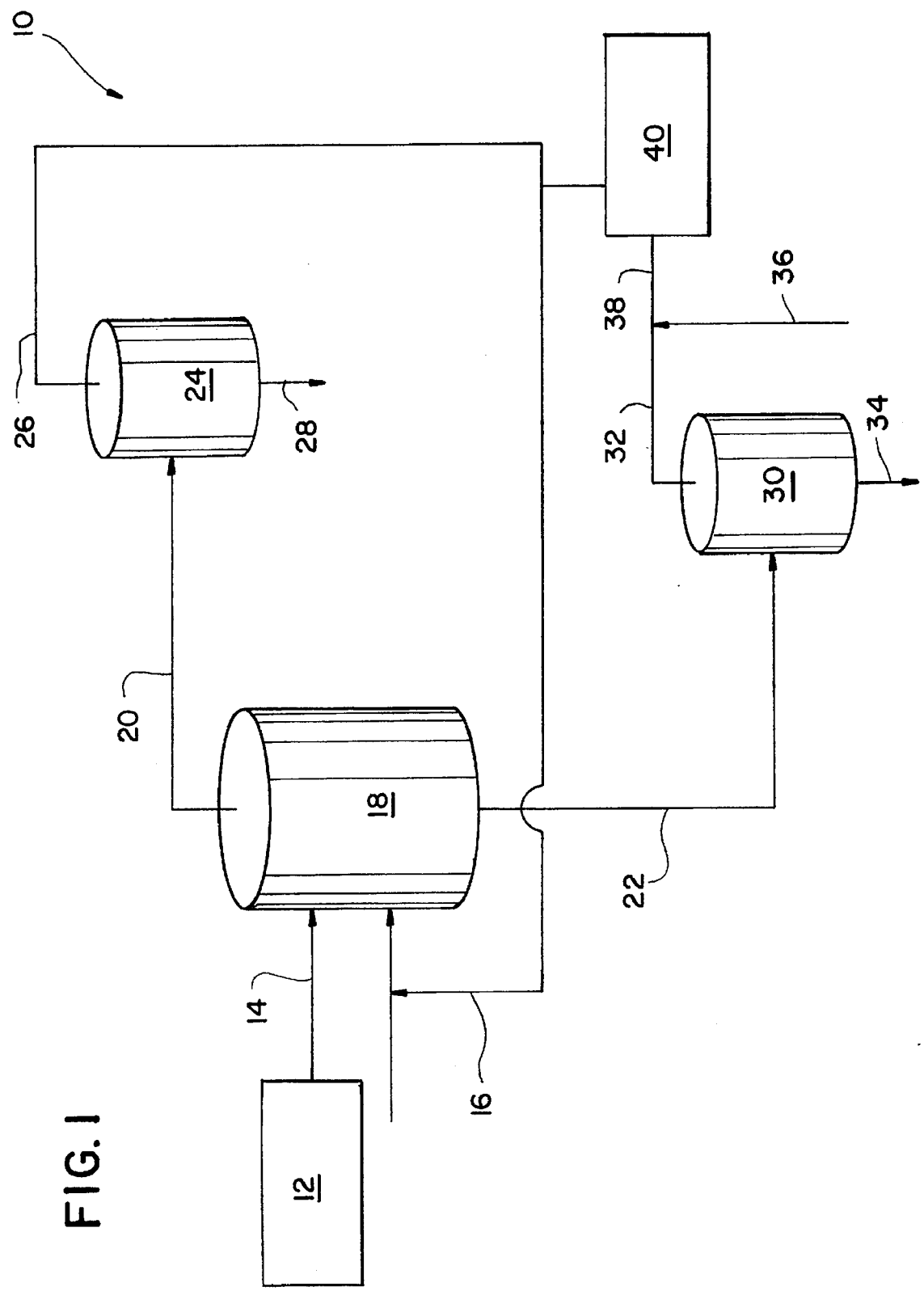
FIG. 1 is a schematic representation of the acid recovery process of the present invention.

Referring to FIG. 1, there is shown an acid recovery process 10. The acid recovery process 10 is associated with the manufacture of a cellulose ester 12. Process 12 generates a weak acid stream 14. Weak acid stream 14 is an aqueous solution of 25–35% by weight organic acid. When the cellulose ester is cellulose acetate, the organic acid is acetic acid. The weak acid stream 14 is sent to a solvent extractor 18. A solvent stream 16, containing extraction liquor, is also fed into an extractor 18. Extractor 18 generates an extractor overhead stream 20 and a raffinate stream 22. Extractor overhead stream 20 generally comprises solvent and organic acid. Stream 20 is fed to still 24 where an overhead stream 26 and a bottom stream 28 are formed. Stream 20 is resolved, by distillation, into solvent and organic acid. Hydrolysis of the solvent is believed to occur principally at this operation in process 10. The overhead stream 26, which is principally solvent, but also includes alcohol and water, may be recycled back into the process via solvent stream 16.

Raffinate stream 22 is fed to a still 30. Raffinate stream 22 comprises solvent, water, and alcohol. Still 30 generates an overhead stream 32 and bottom stream 34. Overhead stream 32 comprises water, alcohol, and solvent in a preferred weight ratio from 2:1:7 to 4:3:13. Concentrated organic acid 36 is fed into stream 32 to form a feed stream 38. While concentrated organic acid is preferred, it is not necessary; it is necessary to have an excess of acid to drive the esterification reaction. The organic acid 36 is added in excess to the alcohol in stream 32, so to drive the esterification reaction. The weight ratio of alcohol in stream 32 to stream 36 is about 1:4 to about 1:14. Feed stream 38 is fed to ion exchange esterification process 40 where alcohol is catalytically converted to solvent. The solvent, converted from the alcohol, may be recycled into the acid recovery process 10 by inclusion with solvent stream 16. Process 40 preferably is sized to balance the generation of alcohol in process 10. Further details regarding the operation of ion exchange esterification process 40 are discussed below by way of examples illustrating several embodiments.

Figure 2:
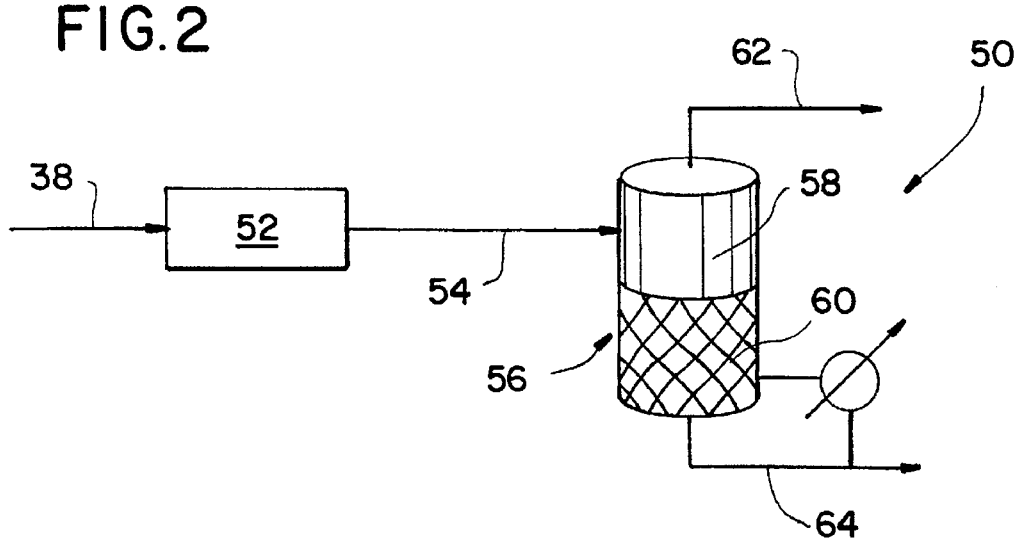
FIG. 2 is a schematic representation of a first embodiment of the ion exchange esterification process.

Referring to FIG. 2, a first embodiment 50 of the ion exchange esterification process 40 is shown. Process 50 utilizes a reactive distillation scheme for the catalytic esterification, via ion exchange resins, of alcohol to solvent. Feed stream 38 is fed into a resin bed 52. Resin bed 52 contains ion exchange resins to reduce or remove any ion contaminates in stream 38 which may poison the ion exchange resins contained in reactive distillation column 56. Resin bed 52 is optional, but preferred. Stream 54, from resin bed 52, is fed into reactive distillation column 56. Column 56 produces a stream 62 which is rich in solvent and a bottom stream 64. Stream 62 may be recycled into process 10. Stream 64 may be recycled into process 10.

Regarding resin bed 52, the ion exchange resin may be the same as that used in column 56. On a unit of feed per hour (units) basis, resin bed 52 should contain about 1.4–1.7 units of resins for a one year service life. The amount of resin may vary depending upon, for example, the amount of ion contamination in the feed stream, the amount of ion removal desired, service life of the bed, and the like. Rohm & Haas AMBERLYST® 15 resin is preferred. Resin bed 52 has an operating temperature of about 30°–60° C.

Regarding reactive distillation column 56, it comprises packing 58 (i.e., inert packing) in the top portion of the column 56 and ion exchange resins 60 (held in catalytic packing) in the bottom portion of the column 56. The packing 58 is sufficient to create about 24 theoretical stages. For one unit of feed per hour, column 56 should contain about 0.45–0.60 units of ion exchange resin 60. The amount of resin is based upon the minimum theoretical amount needed, more may be used as is well known. Rohm & Haas' AMBERLYST® 36 resin is preferred. Column 56 is operated at a pressure of about 0–2 psig, a top temperature of about 60°–85° C., and a bottom temperature of about 102°–110° C. The overhead stream 62 comprises water, alcohol, and solvent in a weight ratio of about 2:1:17 (all alcohol and solvent are carried out overhead). The bottom stream comprises water and unreacted organic acid.

Figure 3:
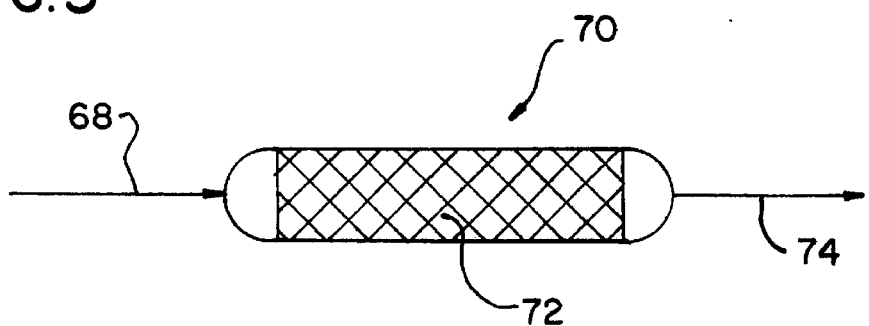
FIG. 3 is a schematic representation of a second embodiment of the ion exchange esterification process.

Referring to FIG. 3, a second embodiment 70 of the ion exchange esterification process 40 is shown. Process 70 utilizes a fixed bed reactor for the catalytic esterification, via ion exchange resins, of alcohol to solvent. Feed stream 68 is fed into a fixed bed reactor 72. Feed stream, prior to the addition of organic acid stream 36, comprises water, alcohol, and solvent in a weight ratio of about 11:7:2. Reactor 72 catalytically converts alcohol to solvent. The weight ratio of alcohol to solvent in stream 68 is about 1:11 to 1:14. The product stream 74 may be recycled into process 10.

Regarding fixed bed reactor 72, it contains, on a unit feed basis, about 2.3 units of resin. The amount of resin is based upon the minimum theoretical amount needed, more may be used as is well known. Rohm & Haas' AMBERLYST® 16 is preferred. Reactor 72 has an operating temperature of about 60° C.

Figure 4:
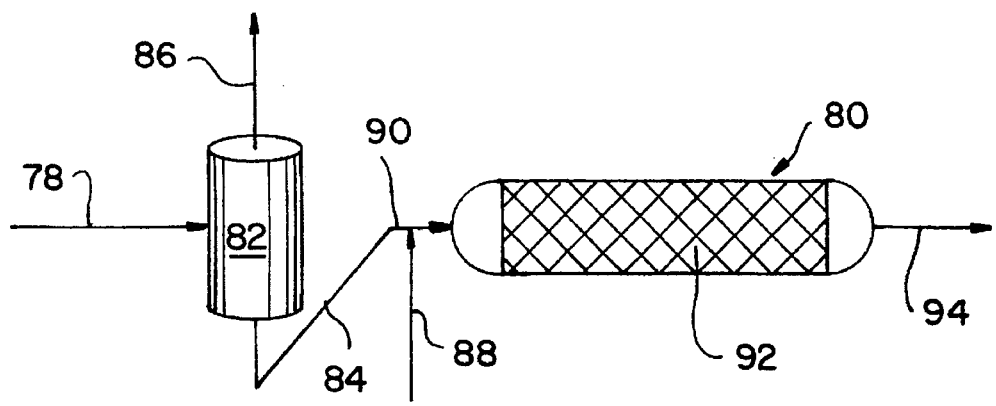
FIG. 4 is a schematic representation of a third embodiment of the ion exchange esterification process.

Referring to FIG. 4, a third embodiment 80 of the ion exchange esterification process 40 is shown. Process 80 utilities a concentrator (i.e., still(s)) 82 and fixed bed reactor 92. Stream 78 is concentrated, via distillation, in still 82. The overhead stream 84 is mixed with excess (concentrated) organic acid stream 88 to form feed stream 90. Stream 90 is fed to reactor 92 which catalytically converts the alcohol to solvent. The product is discharged via line 94 and may be recycled into process 10.

Stream 78 comprises water, alcohol, and solvent in a weight ratio of about 11:7:2. Stream 84 comprises water, alcohol, and solvent in a weight ratio of about 1:7:2. Concentrator 82 operates at a top temperature of about 60°–80° C., a bottom temperature of about 100°–105° C., and a pressure of 0–2 psig. Stream 88 is sized so that it contains about 4–7 times the amount of acid as the amount of alcohol in stream 84.

Regarding fixed bed reactor 92, it contains, on a unit feed basis, about 1.6 units of resin. The amount of resin is based upon the minimum theoretical amount needed, more may be used as is well known. AMBERLYST® 16 is preferred. Reactor 92 has an operating temperature of about 60° C. Stream 94 comprises water, alcohol, solvent, and acid (acetic acid) on a weight ratio of about 1:1:4:14.

The present invention may be embodied in other specific forms without departing from the spirit or essential attributes thereof and, accordingly, reference should be made to the appended claims, rather than to the foregoing specification, as indicating the scope of the invention.

We claim:

1. A process for the recovery of the extraction solvent used in recovery of an organic acid, the organic acid being generated from the manufacture of a cellulose ester, comprising the steps of:

removing the acid from the manufacture of the cellulose ester, the acid being in the form of a weak acid stream comprising organic acid and water;

solvent extracting the weak acid stream and thereby forming a first overhead stream and a raffinate stream, the raffinate stream comprising solvent, water, and alcohol, the alcohol being produced in the recovery process by hydrolysis of solvent after the solvent extraction step, the first overhead stream comprising organic acid, the organic acid being recycled into the manufacture of the cellulose ester;

resolving the raffinate stream into a second overhead stream and a bottom stream, the second overhead stream comprising water, alcohol, and solvent;

adding excess organic acid to the second overhead stream to form a feed stream;

catalyzing, via ion exchange resins, the feed stream, and thereby esterifying a portion of alcohol to solvent; and recycling the last-mentioned solvent into the recovery process.

2. The process of claim 1 wherein catalyzing the feed stream comprises reactively distilling the feed stream.

3. The process of claim 1 wherein catalyzing the feed stream comprises reacting the feed stream in an ion exchange bed.

4. The process of claim 3 wherein catalyzing the feed stream comprises concentrating the overhead stream to form an enriched overhead stream, adding excess organic acid to said enriched overhead stream to form an enriched feed stream; and reacting the enriched feed stream in an ion exchange bed.

5. The process of claim 1 wherein the solvent is selected from the group consisting of organic esters, ketones, alkanes, ethers, and combinations thereof.

6. The process of claim 1 wherein the alcohol is selected from the group consisting of methanol, ethanol, isopropyl alcohol, and combinations thereof.

7. The process of claim 1 wherein the organic acid is acetic acid.

8. A process for the recovery of the extraction solvent used in recovery of acetic acid, the acetic acid being generated from the manufacture of cellulose acetate, comprising the steps of:

removing the acetic acid from the manufacture of the cellulose acetate, the acid being in the form of a weak acid stream comprising acetic acid and water;

solvent extracting the weak acid stream and thereby forming a first overhead stream and a raffinate stream, the raffinate stream comprising solvent, water, and alcohol, the solvent being selected from the group consisting of methyl acetate, ethyl acetate, isopropyl acetate, and mixtures thereof, the alcohol being produced in the recovery process by hydrolysis of solvent after the solvent extraction step, the alcohol being selected from the group consisting of methanol, ethanol, isopropyl alcohol and mixtures thereof, the first overhead stream comprising acetic acid, the acetic acid being recycled into the manufacture of the cellulose acetate;

resolving the raffinate stream into a second overhead stream and a bottom stream, the second overhead stream comprising water, alcohol, and solvent;

adding excess acetic acid to the second overhead stream to form a feed stream;

catalyzing, via ion exchange resins, the feed stream, and thereby esterifying a portion of alcohol to solvent; and recycling the last-mentioned solvent into the recovery process.

* * * * *